(12) United States Patent
Lonky

(10) Patent No.: US 6,496,718 B1
(45) Date of Patent: Dec. 17, 2002

(54) BODY CAVITY LIGHT USING DIFFUSE LIGHT SOURCE

(75) Inventor: Martin L. Lonky, Rancho Palos Verdes, CA (US)

(73) Assignee: The Trylon Corporation, Torrance, CA (US)

( * ) Notice: Subject to any disclaimer, the term of this patent is extended or adjusted under 35 U.S.C. 154(b) by 0 days.

(21) Appl. No.: 09/570,257

(22) Filed: May 12, 2000

(51) Int. Cl.[7] .................................................. A61B 6/00
(52) U.S. Cl. ....................................... 600/476; 600/477
(58) Field of Search ................................... 600/476, 477

(56) References Cited

U.S. PATENT DOCUMENTS

| | | |
|---|---|---|
| D289,926 S | 5/1987 | Lonky |
| 5,036,853 A | 8/1991 | Jeffcoat et al. |
| 5,179,938 A | 1/1993 | Lonky |
| 5,329,938 A | 7/1994 | Lonky |
| 5,465,709 A | 11/1995 | Dickie et al. |
| 5,601,549 A | 2/1997 | Miyagi |
| 5,800,350 A * | 9/1998 | Coppleson et al. ......... 600/372 |
| 5,814,041 A * | 9/1998 | Anderson et al. ............ 606/15 |
| 5,957,917 A * | 9/1999 | Doiron et al. ............... 606/15 |
| 5,989,184 A | 11/1999 | Blair |
| 6,208,887 B1 * | 3/2001 | Clarke ......................... 600/476 |
| 6,217,512 B1 * | 4/2001 | Salo et al. ................... 600/160 |
| 6,332,092 B1 * | 12/2001 | Deckert et al. ............. 600/476 |

* cited by examiner

Primary Examiner—Marvin M. Lateef
Assistant Examiner—Devaang Shah
(74) Attorney, Agent, or Firm—Pillsbury Winthrop LLP

(57) ABSTRACT

An apparatus for performing medical examinations of tissue and a method of performing such examinations are described. The apparatus comprises a modified fiber-optic light source, wherein the modification allows for the creation of a diffuse light source. The diffuse light source produces omni-directional light in the green-blue-white spectrum, which can be used to photo-differentiate healthy from non-healthy tissues based on the absorptivity of the tissue under examination. The luminous element of the apparatus may be miniaturized, and take on shapes which may be usefully employed, including by insertion into a body cavity to be examined. The diffuse light source may be used in conjunction with a speculum, as well as with other endoscopic instrumentation, such as specula, anoscopes, and the like, for application in both diagnostic and surgical procedures. The method of performing examinations using the apparatus is also described.

33 Claims, 3 Drawing Sheets

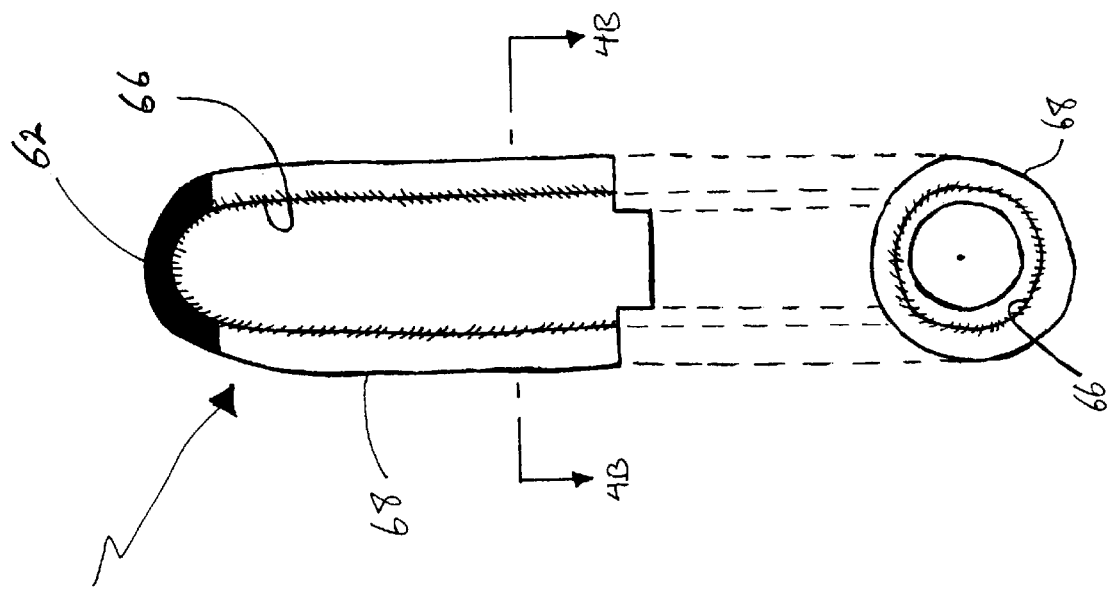
FIG. 4A
FIG. 4B
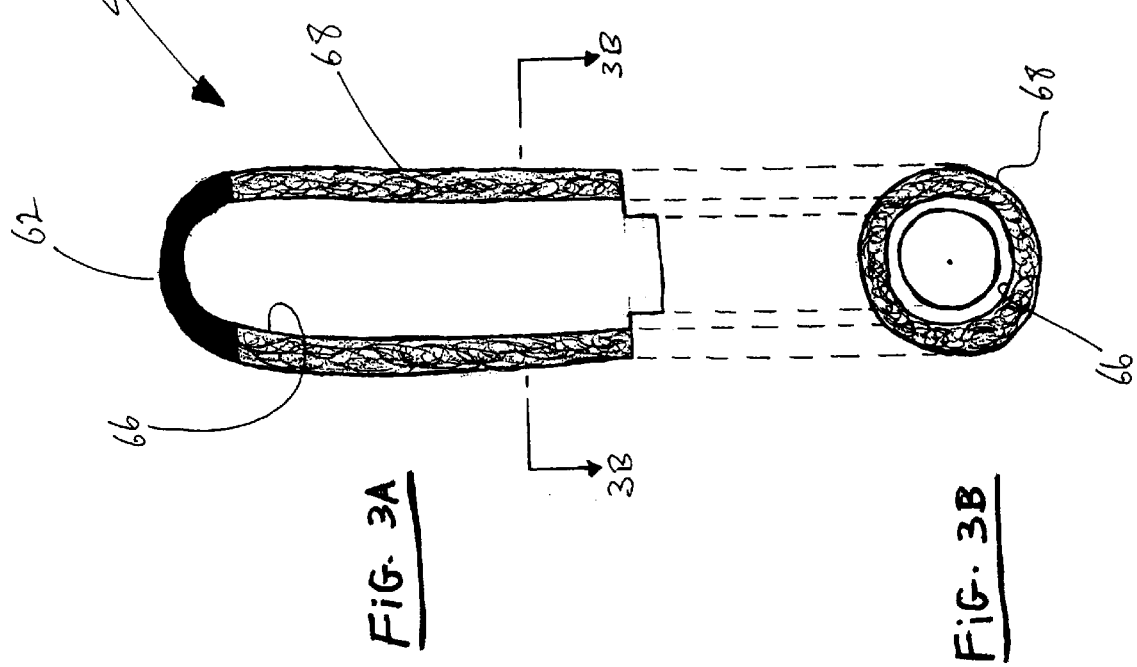
FIG. 3A
FIG. 3B

BODY CAVITY LIGHT USING DIFFUSE LIGHT SOURCE

BACKGROUND OF THE INVENTION

1. Field of the Invention

This invention is in the field of medical devices and methods, and more particularly, directed to the use of particular light sources for diagnosis of various abnormalities, as well as for regular examinations, including procedures performed in conjunction with endoscopes, such as specula, anoscopes and sigmoidoscopes, and the like. This invention also relates to a new method for performing tissue examinations (using vaginal exams as a working example) to greatly improve the accuracy of detecting various disorders, and new devices for performing the improved exams.

2. Art Background

As used herein the phrase "diffuse light" refers to light that is transmitted omni-directionally, and the term "diffuse light source" refers to a light source that transmits an omni-directional light.

A typical gynecological exam or gyn exam comprises the use of a speculum, a visual examination of the interior cavity and related structures, palpation of the pelvic region, and a pap smear. The visual examination is typically performed using a gooseneck lamp or even a flashlight, often without any use of magnification, although magnification has certainly been available in the medical field in other areas, such as microsurgery. There are several disadvantages to this procedure.

First, because a projecting light source is used, the ability to visualize abnormalities or areas of concern is diminished since there may be shadows or glare which distort the appearance of the area. In visual examinations where an absorption-based, photo-differentiation technique is used, such glare or, more generally, specular reflection, may completely thwart the effort to establish a more effective diagnostic procedure. More specifically, in the best-case scenario, the resultant glare mimics the reflection of light from dense or diseased nuclei, thus creating a large amount of diagnostic noise and false positives (i.e., indicating a problem when there is nothing wrong). At worst, the glare is so intense as to completely saturate the visualization/ examination and prevent the examiner from identifying any cellular dysplasia whatsoever.

Second, because an external light source is used, the emitted light is not evenly disbursed which, again, may cause glare and distortion of the area under examination. Third, because the light source is incandescent, it gets hot and cannot be placed close enough to the patient without burning or uncomfortably heating the area being examined. Finally, the light spectrum of the light source (generally white light) is not the most advantageous for viewing the various abnormalities to be detected.

If the visual examination does not detect the abnormalities, a Pap smear may detect them. However, the Pap smear may be inaccurate as the analysis of a Pap smear is typically performed by an outside laboratory and relies heavily on the occurrence of an exfoliated cell from dysplastic lesions, which does not always occur. Consequently, the false negative rate for Pap smears (indicating nothing wrong, when there is a problem) has been shown to be as high as 50%.

If abnormalities are detected, the patient is brought in a second time for a more detailed examination using a colposcope. This device is a binocular microscope which is placed near the patient. A bright light (blue/green filtered white incandescent light) is supplied. The operator looks through the eyepieces of the colposcope much like looking through field glasses. This procedure is performed with a vaginal speculum or similar device in place. Some of the colposcopes have camera attachments for still picture photography.

The physician washes the area with 3–5% acetic acid and then examines the tissue for whitened areas after treatment. The acetic acid whitens tissue which is thickened, such as cancer cells. The physician also looks for clusters of blood vessels which may indicate new growth such as cancer.

The effectiveness of this colposcopy procedure in detecting abnormalities is believed to be approximately 85%, and this effectiveness is due in part to the greater degree of experience which physicians who utilize this procedure generally have. It should be noted, however, that the colposcope is difficult to use because of its size, weight, and complexity. Accordingly, it is not available in all medical facilities. It is also very expensive and not at all portable. Moreover, the procedure itself is very expensive, for both patients and medical facilities, in comparison to the Pap smear.

Because colposcopy is a specialized procedure, requiring advanced and comprehensive training on very complicated and expensive apparatus, colposcopy is typically only performed on patients who have had an abnormal screening procedure (i.e., Pap smears or other indications). Such systems have been shown to be useful in the confirmation of Pap test results, as well as in other diagnostic procedures. Various forms and variations of colposcopes are disclosed in U.S. Pat. Nos. 3,994,288; 4,134,637; 4,232,933; 4,652,103; and 4,905,670.

A number of the above-mentioned concerns were addressed by the Speculite® product, an endoscopic instrument that includes a cherniluminescent light source. The Speculite®, as well as the corresponding method of use, are described in U.S. Pat. Nos. 5,179,938, and 5,329,938, assigned to The TRYLON Corporation. As explained in these patents, the chemiluminescent light source provides a portable source of illumination of the body cavity without producing any heat which could damage, or at least be uncomfortable to, the tissue in the body cavity which is being observed with the endoscopic instrument. Moreover, there is no requirement for any electrical source such as a power cord or batteries. This device also disburses light throughout the cavity being observed, rather than focusing light at a specified location.

An additional advantage of endoscopes comprising a chemiluminescent light source is that the entire instrument, including the light source, may be disposed of after use. For other (non-disposable) instruments, the latter may be sterilized, and the chemiluminescent light source disposed of and then replaced to obtain a completely sterile device.

Moreover, since the chemiluminescent light source does not require external power, the endoscopic instrument does not have to be connected to, or powered by, any electrical source and can be stored for substantial periods of time without any loss of function. As such, until the chemiluminescent light source is activated by the combination of the two chemiluminescent components, there is no loss of function. On the other hand, batteries which are used in the operation of standard electrical lights which are used in many traditional devices can deteriorate in function even when not in use over a period of time, particularly under adverse conditions such as high heat and/or humidity. Thus, although the Speculite® does have some anticipated shelf life and may, at times, be somewhat temperature sensitive, this device is nevertheless particularly useful in primitive locations where relatively high temperature and heat may be prevalent and long periods of storage may be required before the device is used as an endoscopic instrument.

The devices shown in U.S. Pat. Nos. 5,179,938 and 5,329,938 provided an endoscopic examination and viewing system that was compact, portable, disposable, shadowless, economical, and efficient. The invention also comprised a method of detection of various cellular abnormalities which was quicker, easier, more economical, simpler, more compact, and which could be performed in an office setting without the need to use colposcopy equipment.

Nevertheless, the Speculite® has drawbacks. First, because of its size, the Speculite® is not amenable to miniaturization, so that the range of endoscopic applications with the Speculite® (e.g., in surgical applications) is limited. Second, the Speculite® has a limited fuel source, so that its use as a light source is limited to a finite duration from the time the light source is ignited. Third, while the chemical components comprising the chemiluminescent light source are sealed in their capsule and are non-toxic, rupture of the capsule and spillage of the chemicals may nevertheless be a concern.

SUMMARY

An embodiment of the present invention is directed to a modified fiber-optic light source, wherein the modification allows for the creation of a diffuse light source. The diffuse light source is comprised of an optic cable, having a diffusing element attached thereto, such that the resulting diffuse light source transmits a diffused light that may be used for illumination and/or examination of tissues (e.g., within body cavities). The diffuse light source may be used in conjunction with a speculum, as well as with other endoscopic instrumentation, such as specula, anoscopes, and the like, for application in both diagnostic and surgical procedures.

These and other features and advantages will become more apparent through the following description. It should be understood, however, that the detailed description and specific examples, while indicating particular embodiments of the invention, are given by way of illustration only and various modifications may naturally be performed without deviating from the spirit of the present invention.

BRIEF DESCRIPTION OF THE DRAWINGS

FIG. 3A shows a side view of one embodiment of a diffusing element.

FIG. 3B shows a cross-sectional view of the diffusing element of FIG. 3A.

FIG. 4A shows a side view of another embodiment of a diffusing element.

FIG. 4B shows a cross-sectional view of the diffusing element of FIG. 4A.

DETAILED DESCRIPTION

An embodiment of the present invention is related to an apparatus which produces diffuse light for the examination of tissue (e.g., within body cavities), thus increasing the likelihood of detection of many visually observable abnormalities, such as lesions, irregular vasculature, exophytic regions, ulcerations and other atypias of the cervix, vaginal cavity and other body cavities, as well as discharges. The luminous element of the apparatus may be miniaturized, and take on shapes which may be usefully employed, including by insertion into the cavity to be examined. The luminous element of the apparatus is of a generally cylindrical shape corresponding to the shape and size of the cavity to be observed, although it may be smaller in diameter than the cavity in order to provide an area to enable the physician to view the tissue to be examined.

Embodiments of the present invention are also directed to a method of detection of various medical disorders by means of modifying a fiber-optic light source to provide a diffuse light source which produces omni-directional light within the blue-green-white wavelength range, shining said omni-directional light onto a tissue, and examining said tissue to detect medical anomalies by identifying healthy tissues, where substantially all of the incident light has been absorbed, and non-healthy tissues, where most of the incident light is reflected, rather than absorbed. For the latter situation, cells in abnormal tissues are known to have more dense nuclei, as well as a higher nucleic-to-cytoplasmic ratio. This causes the white component of the incident light to reflect off the dense nuclear material, thus indicating tissue abnormality. For the method described, the surface of the tissue to be examined may be treated prior to examination with a composition which enhances the visualization of various tissue, such as by coating the surface with dilute aqueous acetic acid. Additionally, a magnification means or scope may be used to enhance the examination.

It will be readily appreciated that the embodiments described herein, as well as other embodiments, can serve as a light source for all endoscopic instruments for illumination and examination of the several body cavities, including, but not limited to, the vaginal, anal, and oral cavities. In addition, the embodiments can be used in surgical and miniaturized portals throughout the body in surgery.

Figure 1:
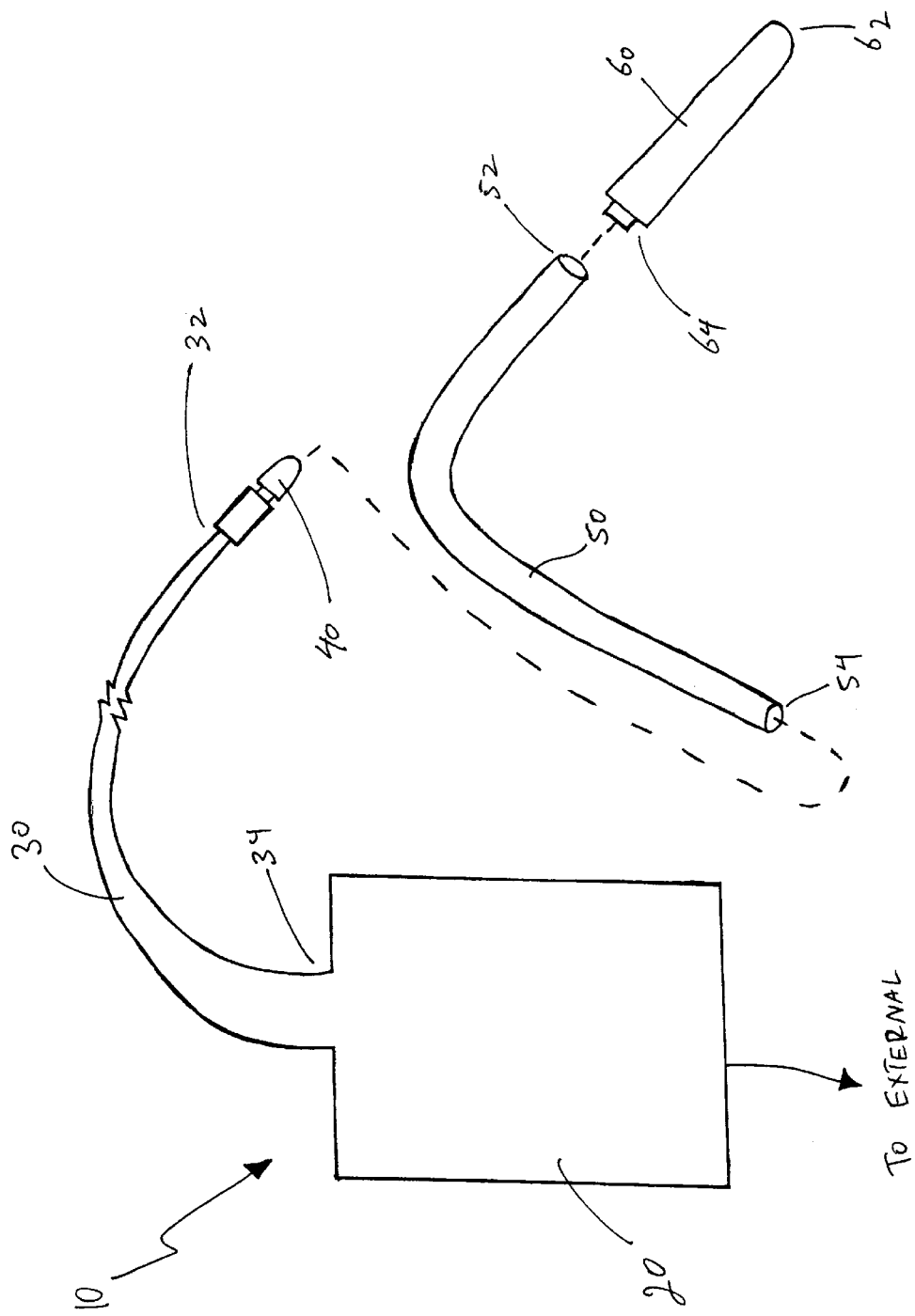
FIG. 1 shows an illustration of the disassembled elements of an embodiment of a diffuse light source.
Figure 2:
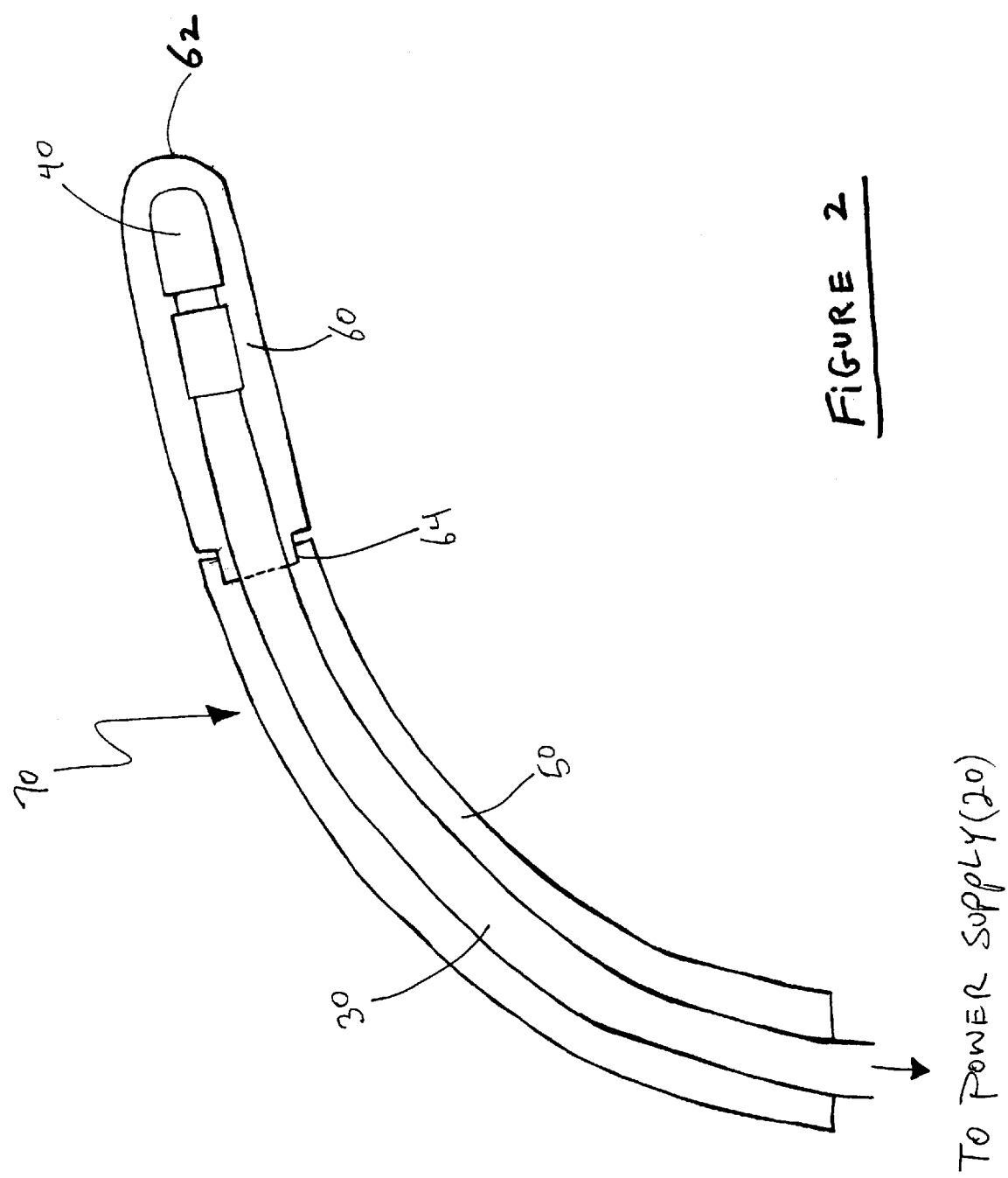
FIG. 2 shows a plan view of an assembled diffuse light source according to an embodiment.

FIGS. 1 and 2 show one embodiment of the present invention. As shown in these figures, a diffuse light source 70 comprises a fiber-optic light source 10 that is modified by, inter alia, a diffusing element 60.

The fiber-optic light source 10 comprises a power supply 20, one end of which is attached to means for connection to an external electrical source, and a second end of which is connected to an optic cable 30. The optic cable has a proximal end 34, that is attached to the power supply 20, and a distal (free) end 32. The latter, in turn, is fixedly attached to a luminous element 40.

The diffuse light source 70 is constructed by the addition of a diffusing element 60 to the fiber-optic light source 10. The diffusing element 60 may be in the shape of a hollow U and made of transparent or translucent material, such as clear plastic. However, materials with similar characteristics that are known to the person skilled in the art may also be used. The diffusing element 60 is made so as to be capable of being slid over, and covering, the luminous element 40. Once the diffusing element has been properly positioned, it is held in place by a restraining member 50. As shown in FIG. 2, the restraining member 50 is a flexible sleeve, having proximal end 54 and distal end 52. In this embodiment, the proximal end 64 of the diffusing element 60 fits snugly into, and is held in position by, the distal end 52 of the flexible sleeve.

The diffusing element 60 serves to scatter focused, unidirectional, high-intensity light that is normally emitted by the luminous element 40 into a diffuse, omni-directional, low-level light within the green-blue-white spectrum. As shown in FIGS. 3A and 3B, in one embodiment, this objective is achieved by frosting the diffusing element 60. In another embodiment, either the inner surface 66, the outer surface 68, or both surfaces of the diffusing element 60 may be abraded, or roughened, to achieve the same goal. FIGS. 4A and 4B depict an embodiment wherein the inner surface 66 of the diffusing element 60 has been abraded.

It has been found that silvering, or blackening, the distal end 62 of the diffusing element 60, so as to block the transmission of light emitted by the luminous element 40 from the distal end 62, maximizes scattering of the emitted light (see FIGS. 3A and 4A). That is, since no clear exit port exists, the emitted light is forced to exit through the sides of the diffusing element 60, thus creating an omni-directional, shadowless light. Specifically, the diffusing element 60 acts to modulate the amplitude of the light emitted by the luminous element 40. This allows in-situ scattering of the emitted light into a diffuse, low-level light which is shadowless/non-reflective (i.e., light that does not cause glare, or specular reflection).

In practice, the examining professional mounts a flexible sleeve 50 onto the optic cable 30 of the fiber-optic light source 10. The flexible sleeve 50 is slid far enough towards the proximal end 34 of the optic cable 30 so that its distal end 52 is positioned at a set distance from the distal end 32 of the optic cable 30. Next, the diffusing element 60 is slid over the luminous element 40 and the distal end 32 of the optic cable 30. The flexible sleeve 50 is then moved distally, so that its distal end 52 engages the proximal end 64 of the diffusing element 60, and a diffuse light source 70 is created. Thus, the diffuse light source 70 is a modified version of the fiber-optic light source 10.

The examining professional then inserts the distal end 62 of the diffusing element 60 into the body cavity to be examined. Since the diffuse light source 70 produces low-level light, the distal end 62 can be placed proximate to the tissue under examination without causing discomfort to the patient. Moreover, the embodiments shown in FIGS. 3A–4B may be used in conjunction with specula or endoscopic instruments, such as those described in U.S. Pat. Nos. 5,179,938, and 5,329,938, the disclosures of which are incorporated herein by reference.

Once at the site of the tissue to be examined, the luminous element 40 is activated, and the tissue is illuminated. Since the resulting diffuse light is of the green-blue-white wavelength range, once the tissue has been illuminated, the examiner can visually distinguish between healthy and diseased tissues based on the level of absorptivity of the tissue. As cells in a tissue devolve from a healthy to pre-cancerous to cancerous state, their nuclei mutate from a relatively dilute consistency, which is absorptive of light, to one that is increasingly dense and, as such, increasingly reflective of light. Put another way, whereas, in a healthy cell, the nucleic-to-cytoplasmic ratio (N/C) is closer to zero, in a cancerous cell, N/C approaches 1.0. Moreover, light within a band comprising at least blue and green wavelengths is best suited to an absorption-based discrimination between healthy and non-healthy tissues.

Using light from this portion of the spectrum, it is then possible to photo-differentiate healthy and diseased tissues by measuring or visualizing increased nucleic-to-cytoplasmic ratios, as indicated by the change in the absorptivity of light in the cells and, thus, in the tissue under examination. Thus, when the examining professional illuminates a tissue with the diffuse light source of the embodiment described herein, the portion of the tissue containing healthy cells will appear dark. That is, substantially all of the light in this region will be absorbed since $N/C<<1.0$. In contrast, portions of the tissue containing pre-cancerous and cancerous cells appear lighter. In these regions, as N/C approaches 1.0, little, if any, of the incident light is absorbed, and substantially all of it is reflected.

Although this approach has been shown to be effective in squamous tissues, there is evidence that it may be successfully applied to other types of tissue, including, but not limited to, columnar and muscle tissues, as well. Also, in order to enhance visualization of the tissue to be examined, the surface of the tissue may be treated prior to examination with a composition, such as dilute aqueous acetic acid. Additionally a magnification means or scope may be used to enhance the examination.

Since the diffuse light source is powered by electricity, the duration of the examination is not limited by a finite fuel source. Also, obviating the need for chemical energy also eliminates the presence of chemical elements in the body. In addition, in contrast to the chemiluminescent light of the Speculite®, there is no requirement that the luminous element include a container large enough to contain a sufficient amount of chemiluminescent material to light the interior of the cavity being examined. As such, the luminous element is capable of being miniaturized, so as to enable its use in surgical and miniaturized portals throughout the body. Moreover, the mechanical elements of the diffuse light source are external to the luminous element (and to the body), and the diffusing element can be made to be disposable. Therefore, after each use, only a small portion of the overall device is thrown away, and only minimal sterilization is required. For these reasons, the present invention is less expensive to produce and to use on a per-use basis.

It will be apparent to a person of ordinary skill in the art that embodiments of the present invention are not limited in their design or application to specific embodiments disclosed herein. Rather, the present invention is intended to encompass all of the embodiments disclosed and suggested herein as defined by the claims appended hereto and any equivalents thereof.

What is claimed is:

1. A diffuse light source for illumination and examination of tissue to detect medical anomalies, comprising a modified fiber-optic light source, wherein the diffuse light source is configured to be disposed proximate said tissue and to produce diffuse, omni-directional, shadow-less light within the green-blue-white spectrum to enable photo-differentiation by direct visual observation of the amount and color of a reflected portion of said light from said tissue.

2. The device of claim 1, wherein the modified fiber-optic light source comprises:
   a power supply;
   an optic cable, wherein the optic cable further comprises a proximal end that is attached to the power supply, and a distal end;
   a luminous element fixedly attached to the distal end of the optic cable;
   a diffusing element that slidably fits over, and covers, the luminous element and the distal end of the optic cable; and
   a restraining member that engages and holds the diffusing element in place.

3. The device of claim 2, wherein the restraining element is a sleeve with a proximal end and a distal end, said sleeve slidably fitting over a length of the optic cable, with the distal end of the sleeve being positioned at a distance proximally from the distal end of said optic cable.

4. The device of claim 3, wherein the sleeve is made of flexible material.

5. The device of claim 3, wherein the diffusing element has a proximal end and a distal end, said proximal end fitting securely into said distal end of said sleeve.

6. The device of claim 2, wherein the diffusing element is substantially in the shape of a hollow U, containing an inner surface and an outer surface.

7. The device of claim 6, wherein the diffusing element is made of frosted material.

8. The device of claim 6, wherein the inner surface of the diffusing element is abraded.

9. The device of claim 8, wherein the outer surface of the diffusing element is further abraded.

10. The device of claim 6, wherein the outer surface of the diffusing element is abraded.

11. The device of claim 2, wherein the diffusing element can be disposably removed after each examination.

12. A diffuse light source for illumination and examination of tissue to detect medical anomalies, comprising a modified fiber-optic light source, wherein the diffuse light source is configured to be disposed proximate said tissue and to produce diffuse, omni-directional, shadow-less light within the green-blue-white spectrum to enable photo-differentiation by direct visual observation of the amount and color of a reflected portion of said light from said tissue, the modified fiber-optic light source comprising:

a power supply;

an optic cable, wherein the optic cable further comprises a proximal end that is attached to the power supply, and a distal end;

a luminous element fixedly attached to the distal end of the optic cable;

a flexible sleeve with a proximal end and a distal end, said sleeve slidably fitting over a length of the optic cable, with the distal end of the sleeve being positioned at a distance proximally from the distal end of said optic cable; and a diffusing element, substantially in the shape of a hollow U and containing an inner and an outer surface, configured to slidably fit over, and cover, the luminous element and the distal end of the optic cable, said diffusing element being disposably removable and having a proximal end and a distal end, said proximal end fitting securely into said distal end of said flexible sleeve, and said flexible sleeve engaging and holding the diffusing element in place.

13. The device of claim 12, wherein the diffusing element is made of frosted material.

14. The device of claim 12, wherein the inner surface of the diffusing element is abraded.

15. The device of claim 14, wherein the outer surface of the diffusing element is further abraded.

16. The device of claim 12, wherein the outer surface of the diffusing element is abraded.

17. A method of performing an examination of tissue to detect medical anomalies, comprising the steps of:

a. providing a diffuse light source comprising a modified fiber-optic light source, wherein the diffuse light source produces diffuse, omni-directional light within the green-blue-white spectrum;

b. placing the diffuse light source proximate to said tissue;

c. shining said omni-directional light upon said tissue; and d. visually examining said tissue using photo-differentiation, wherein the health of said tissue is determined by directly observing the amount and color of a reflected portion of said light from said tissue.

18. The method of claim 17, further comprising the step of pre-treating the surface of the tissue with a composition which enhances the visualization of the tissue.

19. The method of claim 17, wherein the diffuse light source is retained on a speculum.

20. The method of claim 17, wherein the diffuse light source is disposed on an endoscope.

21. The diffuse light source according to claim 1, wherein said reflected portion is the white component of said light when said tissue is diseased.

22. The diffuse light source according to claim 12, wherein said reflected portion is the white component of said light when said tissue is diseased.

23. The method of claim 17, wherein said reflected portion is the white component of said light when said tissue is diseased.

24. The method of claim 17, further including using a magnification means to conduct said visual examination.

25. The method of claim 18, wherein said composition is dilute aqueous acetic acid.

26. A diffuse light source for illumination and examination of tissue to detect medical anomalies, said light source comprising a luminous element and a diffusing element, wherein:

the diffusing element is configured to slidably fit over, and cover, said luminous element, said diffusing element being disposably removable and having a proximal end and a distal end, said distal end being configured to block the transmission of light emitted from said luminous element; and the diffuse light source is configured to be disposed proximate said tissue and to produce diffuse, omni-directional, shadow-less light within the green-blue-white spectrum to enable photo-differentiation by direct visual observation of the amount and color of a reflected portion of said diffuse, omni-directional, shadow-less light from said tissue.

27. The diffuse light source according to claim 26, wherein said distal end of said diffusive element is silvered.

28. The diffuse light source according to claim 26, wherein said distal end of said diffusive element is blackened.

29. The diffuse light source according to claim 26, wherein said reflected portion is the white component of said diffuse, omni-directional, shadow-less light when said tissue is diseased.

30. A method of performing an examination of tissue to detect medical anomalies, comprising the steps of:

a. providing a diffuse light source, said light source producing a diffuse, omni-directional, shadow-less light within the green-blue-white spectrum and including a diffusive element having a distal end, said distal end being configured to block the transmission of light;

b. placing the diffuse light source proximate to said tissue;

c. shining said light upon said tissue; and d. visually examining said tissue using photo-differentiation, wherein the health of said tissue is determined by directly observing the amount and color of a reflected portion of said diffuse, omni-directional, shadow-less light from said tissue.

31. The method of claim 30, wherein said distal end of said diffusive element is silvered.

32. The method of claim 30, wherein said distal end of said diffusive element is blackened.

33. The method of claim 30, wherein said reflected portion is the white component of said diffuse, omni-directional, shadow-less light when said tissue is diseased.

* * * * *